(12) United States Patent
Battles et al.

(10) Patent No.: US 7,232,448 B2
(45) Date of Patent: Jun. 19, 2007

(54) MINIMALLY INVASIVE STITCHING DEVICE

(75) Inventors: Christopher Austin Battles, Hamden, CT (US); David Selvitelli, Suffield, CT (US)

(73) Assignee: Ethicon, Inc. - USA, Somerville, NJ (US)

( * ) Notice: Subject to any disclaimer, the term of this patent is extended or adjusted under 35 U.S.C. 154(b) by 442 days.

(21) Appl. No.: 10/870,498

(22) Filed: Jun. 17, 2004

(65) Prior Publication Data

US 2005/0283170 A1    Dec. 22, 2005

(51) Int. Cl.
  *A61B 17/04* (2006.01)
  *A61B 17/10* (2006.01)
  *A61B 17/08* (2006.01)
(52) U.S. Cl. ............... 606/144; 606/139; 606/148
(58) Field of Classification Search ........ 606/139, 606/144, 145, 147, 148; 289/17; 112/169; 227/67, 68, 71; 128/898
See application file for complete search history.

(56) References Cited

U.S. PATENT DOCUMENTS

| | | | |
|---|---|---|---|
| 4,935,027 A * | 6/1990 | Yoon .................... | 606/148 |
| 5,601,571 A | 2/1997 | Moss | |
| 5,681,333 A * | 10/1997 | Burkhart et al. ........... | 606/148 |
| RE36,020 E | 12/1998 | Moore et al. | |
| 5,928,252 A * | 7/1999 | Steadman et al. .......... | 606/148 |
| 6,059,800 A | 5/2000 | Hart et al. | |
| 6,071,289 A | 6/2000 | Stefanchik et al. | |
| 6,074,404 A | 6/2000 | Stalker et al. | |
| 6,096,051 A | 8/2000 | Kortenback | |
| 6,551,330 B1 * | 4/2003 | Bain et al. .................. | 606/144 |
| 7,118,583 B2 * | 10/2006 | O'Quinn et al. ........... | 606/139 |

FOREIGN PATENT DOCUMENTS

EP    0 599 772 A    6/1994

OTHER PUBLICATIONS

European Search Report regarding Application No. EP 05 25 3760 dated Oct. 4, 2005

* cited by examiner

*Primary Examiner*—Julian W. Woo
(74) *Attorney, Agent, or Firm*—Emil Richard Skula

(57) ABSTRACT

A stitching device useful for implanting suture in tissue, for example, cartilaginous tissue. The device has a frame and an elongated tubular member mounted thereto. A suture capture needle having a suture capture opening extends from a distal end of the tube. A needle cannula having a lumen is slidably mounted in a passage of the tubular member. Actuation of a trigger member pivotally mounted to the frame moves a distal end of the cannula needle and a section of suture contained in a lumen in the cannula needle through the suture capture opening causing the suture section to be retained in the opening.

15 Claims, 5 Drawing Sheets

MINIMALLY INVASIVE STITCHING DEVICE

TECHNICAL FIELD

The field of art to which this invention relates is soft tissue repair, in particular, the repair of cartilaginous with sutures.

BACKGROUND OF THE INVENTION

Injuries that cause damage to cartilage, especially cartilage in the knee, are quite common. The cartilage-damaging injuries can occur during sports, at work, or as a result of accidents such as falls or automobile accidents. Cartilage in the knee joint, such as the meniscus, serves the purpose of both supporting the joint and providing a sliding surface that is engaged by the ends of the bones in the knee. Damage to cartilage in the knee can result in knee instability and pain, and over the long term, may result in deterioration of the articulating surfaces of the bones, which may cause arthritis. Medical science has progressed in the treatment of damaged cartilaginous tissue including that in the meniscus. At one time it was believed that cartilaginous tissue could not heal because of the minimal blood supply that typically is associated with cartilage. A typical surgical procedure involved cutting out all or most of damaged cartilage in order to restore some limited joint function. Presently, it is known that the body can heal damaged cartilaginous tissue. Typically, cartilaginous tissue that is damaged or torn may be approximated allowing the damaged tissue to heal. Various devices and methods are available for repairing damaged cartilaginous tissue. The most basic device is a conventional surgical suture. Using a surgical needle and suture, the damage to the cartilaginous tissue, typically a tear, is approximated and maintained by the suture in a fixed position to effect a repair. Typically, suturing is a procedure utilized in an open surgical procedure.

It is known in this art to use minimally invasive procedures in the knee to repair soft tissue, including cartilage. Various tissue fixation devices and application tools have been developed to allow for arthroscopic repair procedures. One example of a meniscal repair device is a meniscal screw that is inserted across a tear in cartilage to bring or approximate the edges of the tear together. Meniscal screws are disclosed in U.S. Pat. Nos. 5,569,252, 5,730,744 and 6,468,277, which are incorporated by reference. Another type of meniscal repair device is an "H-shaped" fastener. Such fasteners are disclosed in U.S. Pat. Nos. 5,085,661, 5,320,633, 5,467,786, 5,470,337, 5,601,571 and 5,941,439, which are incorporated by reference. A combination suture and back anchor device for repairing a tear in a meniscus is disclosed in U.S. Pat. Nos. 4,994,074, 6,047,826, 6,306,159, 6,319,271 and 6,432,123 which are incorporated by reference.

Although such fasteners are useful in arthroscopic tissue repair procedures, there is a constant need in this art for novel and improved devices and methods for repairing soft tissue such as cartilage. It is desirable when repairing a tear in soft tissue in a joint, such as cartilaginous tissue, to leave behind the least amount of mass required in the implant to do the repair. It is known that suture will typically provide the least mass for an implant. However, it is known that it is difficult and requires significant precautions to emplace suture in cartilaginous tissue in an arthroscopic procedure requiring the passage of needles entirely through the joint capsule and out a secondary posterior incision, then tying the ends together by hand. The risks associated with such a procedure include possibly damaging neurovascular structures by needle punctures or nicks, or by inadvertently looping suture around them.

Accordingly, there is a need in this art for novel stitching devices and methods for repairing soft tissue that are useful in minimally invasive surgical procedures, particularly arthroscopic surgical repair procedures.

SUMMARY OF THE INVENTION

Therefore, a device for stitching tissue in minimally invasive surgical procedures is disclosed. The device is particularly useful for stitching torn cartilaginous tissue in arthroscopic surgical procedures. The device has a hollow frame with an interior opening. A handle is mounted to the frame. A trigger member is pivotally mounted to the handle. An elongated tubular member is mounted to the handle. The tubular member has a distal end, a proximal end and an interior passage. A cannula needle is slidably mounted in the cavity of the frame and the passage of the elongated tube. The cannula needle has a proximal end, a distal end, a lumen, an opening in the distal end, a longitudinal axis and a piercing point extending from the distal end. A needle member is mounted in the passage of the elongated tubular member. The needle member has a proximal end and a distal end. A capture needle extends from the distal end of the needle member. The capture needle has a distal piercing point and a suture capture opening. The capture needle is oriented such that the longitudinal axis of the cannula needle intersects the capture opening. An engagement member is slidably mounted in the interior cavity of the frame. A helical spring is mounted in the cavity such that compression of the spring provides a proximal biasing force against the engagement member. The trigger member engages the engagement member and rotation of the trigger member causes the engagement member and cannula needle to move distally such that the distal end of the cannula needle moves through the suture capture opening.

Yet another aspect of the present invention is a method of emplacing a suture in tissue using the above-described tissue stitching device. These and other aspects and advantages of the present invention will become more apparent from the following description and accompanying drawings.

DETAILED DESCRIPTION OF THE INVENTION

Figure 1:
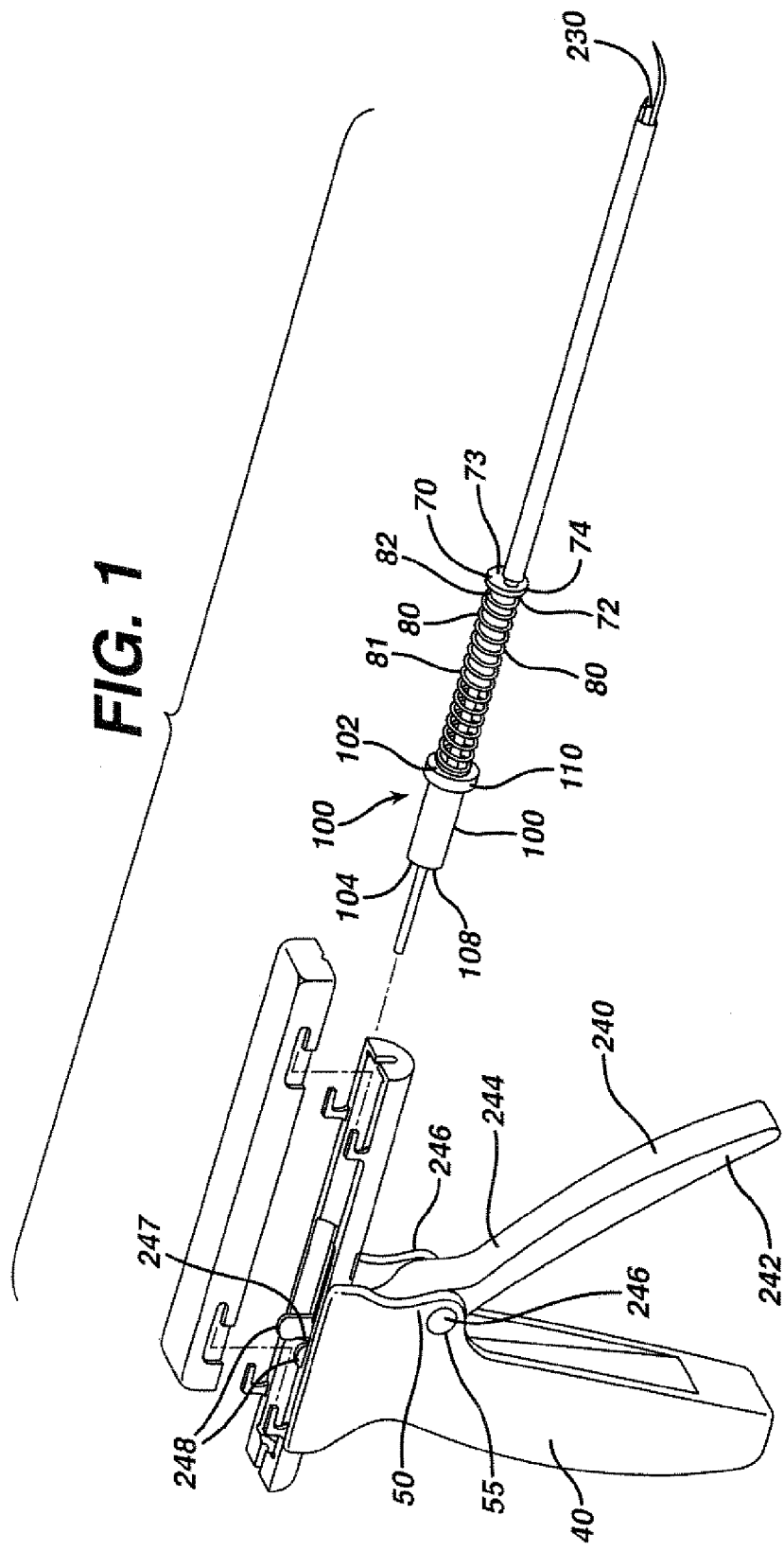
FIG. 1 is a perspective view of a soft tissue suturing device of the present invention.
Figure 2:
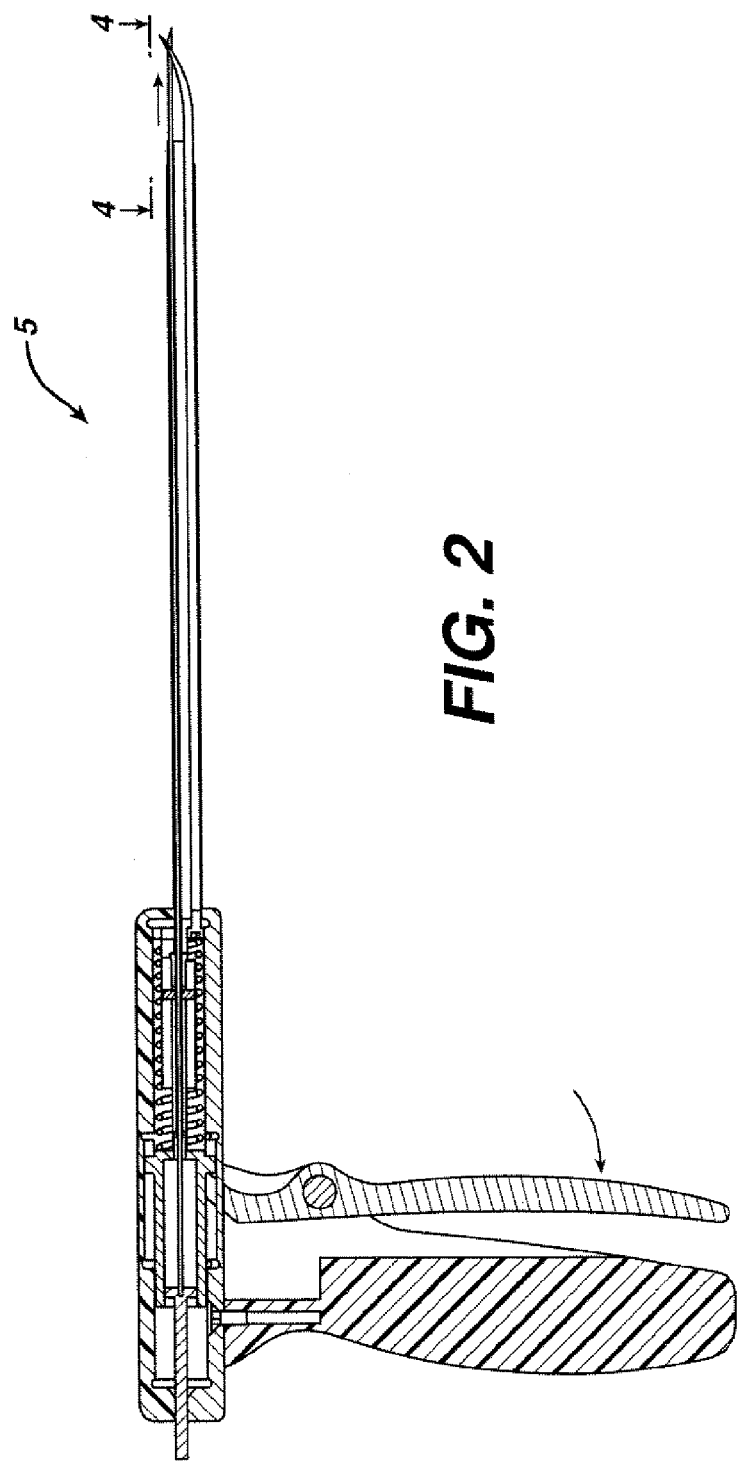
FIG. 2 is a cross-sectional side view of the device of FIG. 1, illustrating the trigger in an actuated position.
Figure 3:
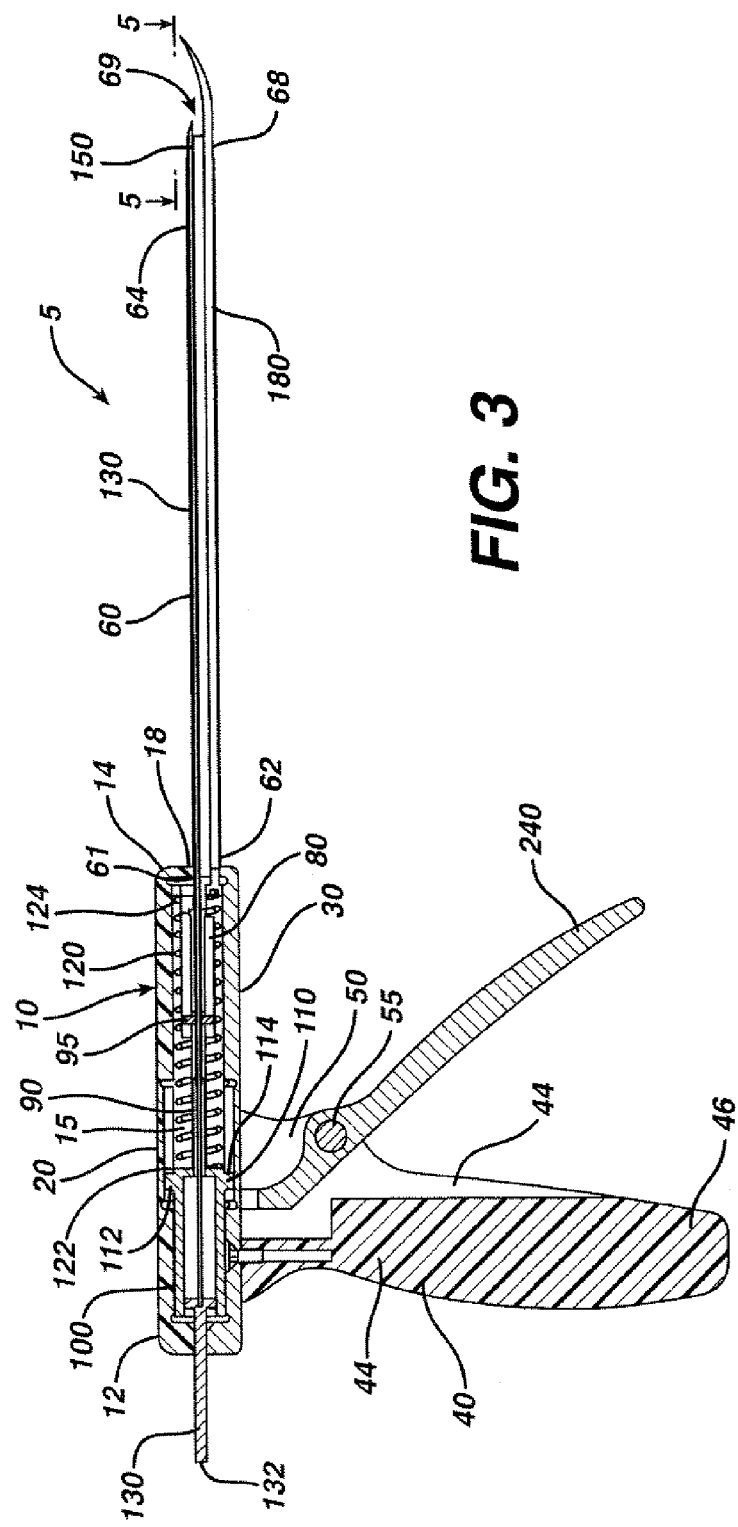
FIG. 3 is a cross-sectional view of the device of FIG. 1., illustrating the device with the trigger in the resting position.
Figure 4:
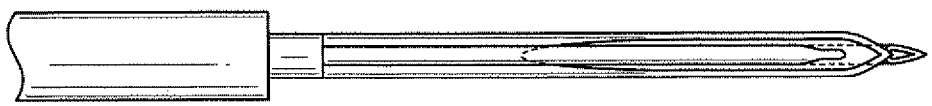
FIG. 4 is a partial top view of the distal end of the instrument of FIG. 1 illustrating the needle cannula in a distal actuated position.
Figure 5:
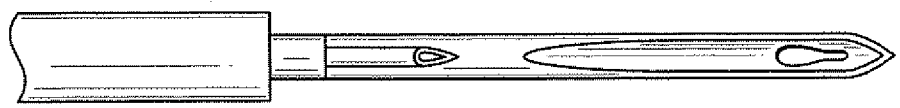
FIG. 5 is a partial top view of the distal end of the instrument of FIG. 1 illustrating the needle cannula in a proximal resting position.

The meniscal repair device 5 of the present invention is illustrated in FIGS. 1-3. The meniscal repair device 5 is seen to have a hollow frame 10. Frame 10 is seen to have proximal end 12, distal end 14, and cavity 15. The frame 10 is also seen to have top section 20 and bottom section 30. Top section 20 is mountable to bottom section 30 via tabs 32 and grooves 22. Extending down from the bottom section 30 is the handle grip 40. Handle grip 40 is preferably hollow and is seen to have inner cavity 42, top 44 and bottom 46. Extending distally from the top 44 are the opposed trigger mounting tabs 50, having pivot pin openings 55. Contained in the distal end 14 of the frame 10 is the opening 18. The opening 18 preferably has a slotted configuration, but may have other geometric configurations as well, and in general will have a configuration capable of accommodating the members the exiting from cavity 15. The tubular member 60 is seen to have proximal end 62, distal end 64, and passage 66. Tubular member 60 is also seen to have proximal opening 61 and distal opening 68. Optionally, although not shown, a proximal section of the proximal end 62 of tubular member 60 may extend though opening 18 into cavity 15 of frame 10. Mounted in cavity 14 adjacent to opening 18 is the disc member 70. Disc member 70 is seen to have proximal face 72, distal face 73, and side 74 and axial opening 79. The spring support member 80 is seen to be a cylindrical member having a proximal end 81, a distal end 82, an inner passage 83 and an outer surface 84. A pair of opposed slots 88 extend from outer surface 84 through to inner passage 83. The distal end 82 is mounted to the proximal face 72 of disc member 70. Plunger rod 90 is seen to be a tubular member having an outer surface 96, distal end 94, proximal end 92, and passage 98, and is slidably mounted in passage 83 of support member 80. Extending from the outer surface 96 are opposed guide members 95 that are engaged in slots 88. The plunger member 100 is also seen to be slidably mounted in cavity 15. Member 100 seen to be a cylindrical member having a distal end 102, a proximal end 104, an outer surface 106 and a passage 108. Extending from the outer surface 106 at the distal end 104 is the engagement collar 110. The engagement collar 110 is an annular member having a proximal face 112 and a distal face 114. Mounted in the passage 108 and extending back out through the proximal end 12 of frame 10 is the push rod engagement member 130 having proximal end 132, distal end 134, and mounted to distal end 134 is the disc member 138. Suture push rod 140 is seen to have proximal end 142 and distal end 144. The proximal end 142 of push rod 140 is mounted to disc member 138. Suture push rod 140 is seen to be slidably mounted in passage 98 of plunger rod 90 and passage 158 of needle cannula 150. Mounted over the spring support member 80 and the plunger rod 90 is the spring member 120. Spring member 120 is preferably a helical spring. Spring member 120 is seen to have proximal end 122, distal end 124 and interior passage 126. The proximal end 122 of spring member 120 is engaged by engagement collar 110, while the distal end 124 engages disc member 70. Needle cannula 150 is seen to be slidably mounted in passage 66 of tubular member 60. Needle cannula 150 is seen to be a tubular member having an inner passage or lumen 158, a proximal end 152, proximal opening 153, distal end 154, and opening 155. The distal end 154 is seen to have a sharpened piercing point 156 extending distally. The proximal end 152 is seen to extend into cavity 14 through opening 18 and through opening 79 in disc member 70 into passage 98 of plunger rod 90 and is mounted to proximal end 102 of plunger member 100. Fixedly mounted in the lumen 66 of the tubular member 60 is the capture needle 180. Capture needle 180 is seen to be an elongated tubular member 182 having proximal end 184 mounted to disc member 70 and distal end 186. Extending out from distal end 186 is the piercing capture member 190 as seen in FIGS. 4 and 5. Capture member 190 preferably has an arcuate configuration. Member 190 is seen to have top 191, bottom 192, proximal end 193, distal end 194, and piercing tip 195 having tip 196 and optional cutting edges 198. Contained in capture member 190 is the suture capture opening 200. Capture opening 200 preferably has a keyhole-shaped configuration, but may have other geometric configurations as well. Opening 200 is seen to have central section 202, which is substantially elliptical but may have other configurations including circular, etc. Tapered engagement opening 205 is seen to be in communication with central section 202. The optional support rod 230 is seen to be fixedly mounted in passage 66 of tubular member 60 between the capture needle 180 and the cannula needle 150. Support rod 230 is seen to have proximal end 232 and distal end 234. The proximal end 232 is mounted to the distal face 73 of disc member 70. Pivotally mounted to the handle mounting tabs 50 of the handle 40 is the trigger member 240. Trigger member 240 is seen to have upper end 244 and lower end 242. The pivot pins 246 are seen to extend laterally out from end 244. The pivot pins 244 are mounted in openings 55 of tab members 50 such that the trigger member 240 is rotatable about the pins 244. Extending from the top of trigger member 240 into cavity 15 are the opposed engagement members 248 of engagement yoke 247.

The instrument 5 of the present invention operates in the following manner. Initially, a first end 305 of a suture 300 is loaded through distal opening 155 of cannula needle 150 into the passage 158 of the cannula needle 150 at distal end 154. The second end 307 of suture 300 is folded back proximally to form a trailing end 310 and a suture loop 315. When the trigger member 240 is pulled proximally it causes the member 240 to rotate about pivot pin members 246. Yoke members 248 then engage engagement collar 110 causing the plunger member 100 and plunger rod 90 to move forward as cannula needle 150 slides forward or distally in passages 83 and 66, while compression spring 80 is compressed causing a biasing force to be exerted proximally against engagement collar 110. Simultaneously, guide members 95 move distally in slots 88. Rotation of trigger member 240 continues until distal end 154 with suture loop 315 moves through opening 200 in capture member 190. This causes the suture loop 315 to be engaged or captured in engagement opening 205 of keyhole opening 200. Release of the trigger member 240 allows the spring member 80 to expand and to move the plunger member 100 and plunger rod 90 along with cannula needle 150 proximally causing the components to revert back to their resting positions and causing the section 305 of suture 150 to disengage from passage 158. If desired or necessary, the first end 305 of the suture 300 may be ejected out of the passage or lumen 158 of cannula needle 150 by pushing distally on the pushrod engagement member 130 which engages and moves suture push rod 140 distally in through passage 98 of plunger rod 90 and through passage or lumen 158 of cannula needle 150 such that the distal end 144 of pushrod 140 engages the first end 305 of the suture 300 contained in lumen 158.

Figure 6:
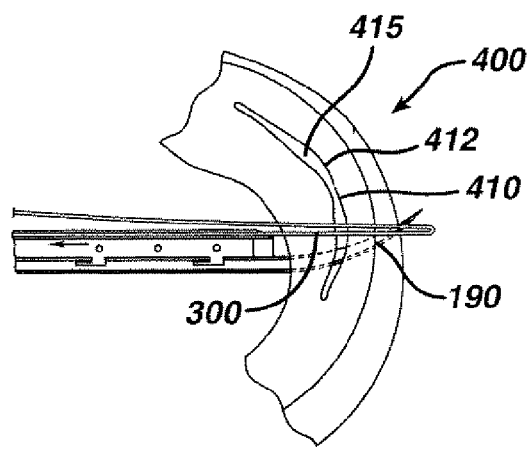
FIGS. 6-8 illustrate the meniscal repair device being used to implant a suture in the cartilage of a knee to effect a repair to a tear in the cartilage.
Figure 7:
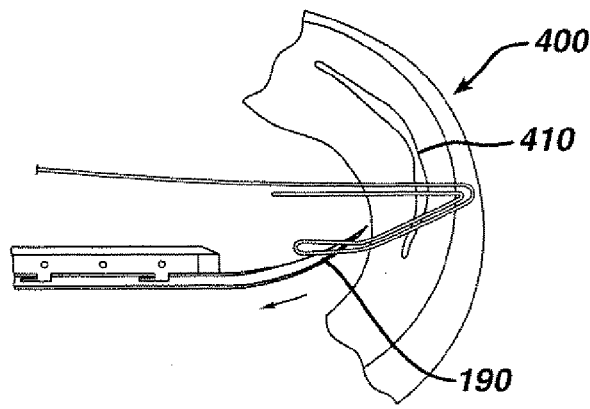
Figure 8:
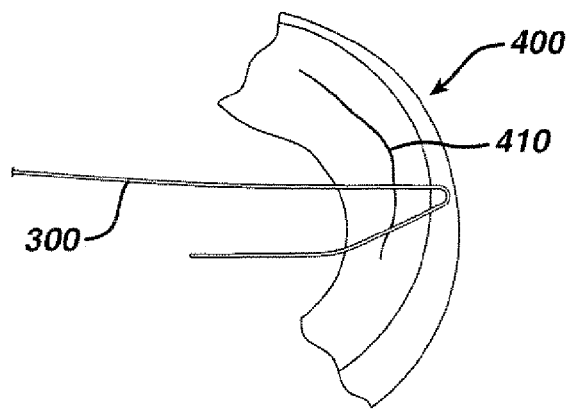

A surgical repair of torn meniscal tissue using the stitching device 5 of the present invention is illustrated in FIGS. 4-6. Meniscus 400 is seen to have tear 410. Tear 410 is seen to have opposed sides 412 separated by opening 415. Prior to accessing the surgical site, the surgeon threads a first end 305 of a conventional suture 300 into the passage or lumen 158 of the cannula needle 150 through distal opening 155 such that a free second end 307 of the suture 300 trails outside of the device 5 and a loop 315 and trailing end 310 are formed. After inserting the distal end 64 of the tubular member 60 through a portal or opening to access the meniscus 400, the surgeon orients the piercing capture member needle 190 adjacent to the tear 410 in the meniscus 400 through which a suture will be implanted. The surgeon then moves or pushes the device 5 distally toward the tear 410 in the meniscus 400 such that the piercing needle member 190 is moved through and partially out of the meniscus 400 about the tear 410. The surgeon then actuates the trigger member 240 causing the distal end 154 of cannula needle 150 and suture loop 315 to move distally though the meniscus 400 about tear 410. As the distal end 154 of the needle 150 exits the meniscus 400 it moves through the capture opening 200 in the capture member 190. The surgeon then releases trigger member 240 causing the suture loop 315 in the capture opening 200 to slide and be retained in the tapered engagement section 205 as the needle 150 moves back out of the meniscus 400 into a resting position. The surgeon then moves the instrument 5 proximally, and as the capture member 190 moves proximally through the meniscus 400, a section of the suture 300 including loop 315 follows and eventually exits the meniscus 400 with the capture member 190. At this stage, the surgeon has emplaced a stitch of suture 300 about the tear 410, and may then tension and knot the suture 300 with a conventional surgical knot, thereby approximating the opposed sides 412 and closing opening 415, completing the repair of tear 410. Alternately, the surgeon may elect to place additional sutures into the meniscus by repeating the procedure and placing conventional surgical knots after the desired number of stitches of suture is emplaced. Although it is preferred to form a loop 315 in suture 100 it is not required, and a single strand of suture 300 may be captured in opening 200.

Although described for use with a cartilage repair procedure, the stitching devices 5 of the present invention may be used in any minimally invasive procedure where it is desired to emplace suture in tissue, including but not limited to arthroscopic, endoscopic and laparoscopic procedures. The devices of the present invention may also be useful in open procedures.

The minimally invasive stitching devices of the present invention may be made from conventional biocompatible materials. The materials include 300 series stainless steels, aluminum and biocompatible plastics such as polycarbonate, ABS, Delrin, etc. The sutures that can be used with the suturing device and methods of the present invention include conventional biocompatible absorbable and nonabsorbable sutures. The suture size will be sufficient to provide effective resistance to any loads or forces placed on the meniscus without breaking. For example, the suture size may range from conventional size about USP #2/0 to about USP #2.

The minimally invasive stitching devices of the present invention are preferably designed to be single use disposable instruments, but may optionally be designed to be reusable, or to be reusable with some disposable components.

The minimally invasive stitching devices of the present invention have many advantages. It is possible using these devices to access a tissue site in a minimally invasive procedure and to implant suture to approximate tissue. The minimally invasive stitching devices have additional advantages including "all inside" repair where the needles do not extend out of the joint capsule, reducing the potential for hitting neurovascular structures in the joint. Also, there is no need for secondary incisions like the "Inside-Out" or Outside-In" suturing techniques. Additionally, there is a more consistent placement of suture than with traditional techniques since there is a fixed distance between the needle, delivering consistent separation between suture holes and a consistent "bite" of tissue.

Although this invention has been shown and described with respect to detailed embodiments thereof, it will be understood by those skilled in the art that various changes in form and detail thereof may be made without departing from the spirit and scope of the claimed invention.

We claim:

1. A tissue stitching device, comprising:
   a hollow frame having an interior cavity;
   a handle mounted to the frame;
   a trigger member pivotally mounted to the handle;
   an elongated tube mounted to the frame, said tube having a distal end, a proximal end and an interior passage;
   a cannula needle slidably mounted in the cavity of the frame and the passage of the elongated tube, said cannula needle having a proximal end, a distal end, a lumen, an opening in the distal end, a longitudinal axis and a piercing point extending from the distal end;
   a needle member mounted in the passage of the elongated tube having a distal end;
   a capture needle extending from the distal end of the needle member, said capture needle having a distal piercing point and a suture capture opening, wherein the capture needle is oriented such that the longitudinal axis of the cannula needle intersects the capture opening;
   an engagement member slidably mounted in the interior cavity of the frame; and,
   a helical spring mounted in the cavity such that compression of the spring provides a proximal biasing force on the engagement member,
   wherein the trigger member engages the engagement member, and rotation of the trigger member causes the engagement member and cannula needle to move distally such that the distal end of the cannula needle moves through the suture capture opening.

2. The stitching device of claim 1, wherein the suture capture opening in the capture needle comprises a keyhole shape.

3. The stitching device of claim 2, wherein the capture opening comprises a suture engagement slot.

4. The stitching device of claim 1, additionally comprising an end of a suture mounted in the passage of the cannula needle.

5. The stitching device of claim 1 wherein the capture needle is curved.

6. The stitching device of claim 1, additionally comprising a suture push rod slidably mounted in the lumen of the cannula needle.

7. The stitching device of claim 1, wherein a top end of the trigger member comprises a yoke.

8. The stitching device of claim 1, additionally comprising a support member in the passage of the tube.

9. A method of placing a suture in tissue, comprising:
   I. providing a tissue stitching device comprising:
   a hollow frame having an interior cavity;
   a handle mounted to the frame;
   a trigger member pivotally mounted to the handle;
   an elongated tube mounted to the frame, said tube having a distal end, a proximal end and an interior passage;
   a cannula needle slidably mounted in the cavity of the frame and the passage of the elongated tube, said cannula needle having a proximal end, a distal end, a lumen, an opening in the distal end, a longitudinal axis and a piercing point extending from the distal end;

a needle member mounted in the passage of the elongated tube having a distal end;

a capture needle extending from the distal end of the needle member, said capture needle having a distal piercing point and a suture capture opening, wherein the capture needle is oriented such that the longitudinal axis of the cannula needle intersects the capture opening;

an engagement member slidably mounted in the interior cavity of the frame; and, a helical spring mounted in the cavity such that compression of the spring provides a proximal biasing force on the engagement member, wherein the trigger member engages the engagement member, and rotation of the trigger member causes the engagement member and cannula needle to move distally such that the distal end of the cannula needle moves through the suture capture opening;

II. loading an end of a suture in the lumen of the cannula needle

III. moving the capture needle through tissue;

IV. pulling the trigger member to move the distal end of the cannula needle and a section of the suture through tissue such that the section of suture is engaged in part by the suture capture opening; and, V pulling the device back proximally to pull the capture needle and the section of suture out from the tissue, thereby emplacing a stitch of suture in the tissue.

10. The method of claim 9, wherein the suture capture opening in the capture needle comprises a keyhole shape.

11. The method of claim 10, wherein the capture opening comprises a suture engagement slot.

12. The method of claim 9, wherein the capture needle is curved.

13. The method of claim 9, wherein the stitching device additionally comprises a suture push rod slidably mounted in the lumen of the cannula needle.

14. The method of claim 9, wherein a top end of the trigger member comprises a yoke.

15. The method of claim 9, wherein the stitching device additionally comprises a support member in the passage of the tube.

* * * * *